United States Patent [19]

Beriger et al.

[11] Patent Number: 5,648,487
[45] Date of Patent: Jul. 15, 1997

[54] PROCESS FOR THE PREPARATION OF AMINOTRIAZINE DERIVATIVES

[75] Inventors: Ernst Beriger, Allschwil; Haukur Kristinsson, Bottmingen, both of Switzerland

[73] Assignee: Ciba-Geigy Corporation, Tarrytown, N.Y.

[21] Appl. No.: 460,474

[22] Filed: Jun. 2, 1995

Related U.S. Application Data

[60] Continuation-in-part of Ser. No. 221,303, Mar. 31, 1994, Pat. No. 5,446,154, which is a division of Ser. No. 991,672, Dec. 16, 1992, Pat. No. 5,324,842, which is a continuation-in-part of Ser. No. 612,753, Nov. 13, 1990, abandoned.

[30] Foreign Application Priority Data

Nov. 15, 1989 [CH] Switzerland .................. 4107/89

[51] Int. Cl.$^6$ ..................................... C07D 253/06
[52] U.S. Cl. ........................................... 544/182
[58] Field of Search .................................. 544/182

[56] References Cited

U.S. PATENT DOCUMENTS

| | | | |
|---|---|---|---|
| 4,931,419 | 6/1990 | Kristinsson | 514/242 |
| 4,996,325 | 2/1991 | Kristinsson | 548/132 |
| 5,179,094 | 1/1993 | Kristiansen et al. | 544/182 |

FOREIGN PATENT DOCUMENTS

79/16515  8/1968  Japan .

OTHER PUBLICATIONS

Chem. Abst. 83:131552Z, (1975) Hetzheim et al.
Chem. Abst. 67:6449v, (1967) Hetzheim et al.
Chem. Abst. 75:129769K (1971) Hetzheim et al.
Chem. Abst. 91:211409g (1979) Takano.
Magnetic Resonance in Chemistry, "$^{15}$N and $^{13}$C NMR Study, etc", Fritz et al., vol. 28, 331–336 (1990).

*Primary Examiner*—John M. Ford
*Attorney, Agent, or Firm*—Marla J. Mathias; William A. Teoli, Jr.

[57] ABSTRACT

A process for the preparation of a compound of the formula

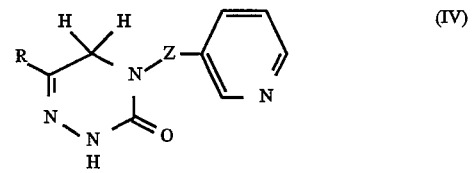 (IV)

where Z and R are defined herein. A compound of formula II

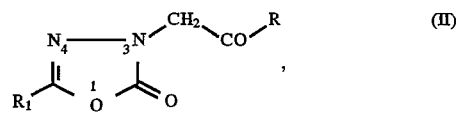 (II)

where $R_1$ defined herein, is reacted with hydrazine hydrate and then subjected to hydrolysis to form the compound of formula I

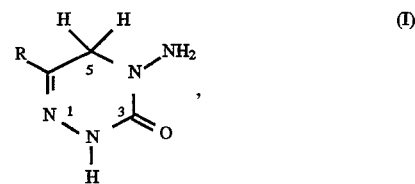 (I)

and the compound of the formula I is reacted with the aldehyde of the formula

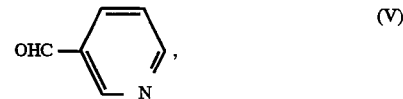 (V)

into the resulting compound of the formula IV.

13 Claims, No Drawings

PROCESS FOR THE PREPARATION OF AMINOTRIAZINE DERIVATIVES

This is a continuation-in-part of Ser. No. 08/221,303, filed Mar. 31, 1994, now U.S. Pat. No. 5,446,154, which is a divisional of Ser. No. 07/991,672, filed Dec. 16, 1992, now U.S. Pat. No. 5,324,842, which is a continuation-in-part of Ser. No. 07/612,753, filed Nov. 13, 1990, now abandoned. Each of these prior applications as well as priority Swiss Application No. 4107/89-7 filed Nov. 15, 1989 are incorporated by reference herein.

The present invention relates to a novel process for the preparation of 4-amino-3-oxo-2,3,4,5-tetrahydro-1,2,4-triazines, to starting materials and intermediates used in this process and to the use of these starting materials and intermediates in this process.

The invention relates to a process for the preparation of a compound of formula

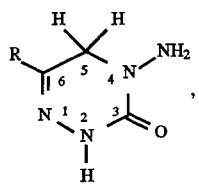
(I)

wherein R is hydrogen, $C_1$–$C_6$alkyl, $C_3$–$C_6$cycloalkyl, $C_1$–$C_4$alkyl substituted by from 1 to 9 halogen atoms or by from 1 to 3 radicals selected from the group consisting of $C_1$–$C_3$alkoxy, $C_1$–$C_3$alkylthio and phenyl, phenyl or phenyl substituted by from 1 to 3 radicals selected from the group consisting of halogen, methyl, ethyl, methoxy, methylthio and nitro, which process comprises reacting with hydrazine hydrate a compound of formula

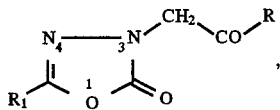
(II)

wherein $R_1$ is hydrogen, $C_1$–$C_4$alkyl, $C_3$–$C_6$cycloalkyl, $C_1$–$C_4$alkyl substituted by from 1 to 9 chlorine atoms, $C_1$–$C_3$alkoxy, $C_1$–$C_3$alkylthio, $C_1$–$C_3$alkylsulfinyl, $C_1$–$C_3$alkylsulfonyl, phenyl, phenyl substituted by from 1 to 3 radicals selected from the group consisting of halogen, methyl, ethyl, methoxy, methylthio and nitro, or pyridyl, and R is as defined in formula I; and subjecting the resulting compound of formula

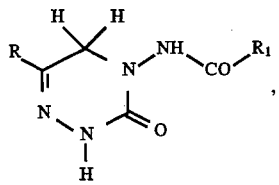
(III)

wherein the substituents R and $R_1$ are as defined in formulae I and II, to hydrolysis, preferably acid hydrolysis.

The present process is preferably used for the preparation of compounds of formula I wherein R is methyl, ethyl, isopropyl, tert.-butyl or cyclopropyl. The process is preferably carried out using as starting materials compounds of formula II wherein $R_1$ is $C_1$–$C_4$alkyl.

A further aspect of the present invention is a process for the preparation of a compound of the formula

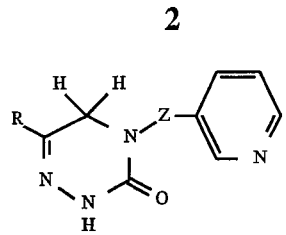
(IV)

wherein R is hydrogen, $C_1$–$C_6$alkyl, $C_3$–$C_6$cycloalkyl, $C_1$–$C_4$alkyl substituted by from 1 to 9 halogen atoms or by from 1 to 3 radicals selected from the group consisting of $C_1$–$C_3$alkoxy, $C_1$–$C_3$alkylthio and phenyl, phenyl or phenyl substituted by from 1 to 3 radicals selected from the group consisting of halogen, methyl, ethyl, methoxy, methylthio and nitro, and Z is —N=CH— or —NH—$CH_2$—, which process comprises converting a compound of the formula III, wherein R and $R_1$ are as defined above, by acid hydrolysis into a compound of the formula I, wherein R is as defined above, reacting the said compound of the formula I with the aldehyde of the formula

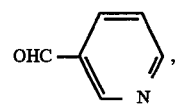
(V)

and, if desired, converting the resulting compound of the formula IV, wherein Z is —N=CH— by selective reduction into a compound of the formula IV wherein Z is —NH—$CH_2$—.

A further aspect of the present invention is a process for the preparation of a compound of the formula IV, wherein R and Z are as defined in the formula IV above, which process comprises reacting a compound of the formula II, wherein the substituents R and $R_1$ are as defined above, with hydrazine to give a compound of the formula III, wherein the substituents R and $R_1$ are as defined above, converting the said compound of the formula III by acid hydrolysis into a compound of the formula I, wherein the substituent R is as defined above, and reacting the compound of the formula I with the aldehyde of formula V, and, if desired, converting the resulting compound of the formula IV, wherein Z is —N=CH— by selective reduction into a compound of the formula IV wherein Z is —NH—$CH_2$—.

The compounds of the formula IV are distinguished by pronounced insecticidal and acaricidal activity. Such pesticidal compounds are, for example, 4-[(pyrid-3-yl)-methylene-amino]-3-oxo-6-methyl-2,3,4,5-tetrahydro-1,2,4-triazine, 4-[(pyrid-3-yl)-methyleneamino]-3-oxo-6-cyclopropyl-2,3,4,5-tetrahydro- 1,2,4-triazine, 4-[(pyrid-3-yl)-methylamino]-3-oxo-6-isopropyl-2,3,4,5-tetrahydro-1,2,4-triazine and 4-[(pyrid-3-yl)-methylamino]-3-oxo-6-tert.-butyl-2,3,4,5-tetrahydro- 1,2,4-triazine. Such pesticidal compounds, their preparation and use are described in EP Patent Application No. 314,615.

The process according to the invention can be illustrated by the following reaction scheme, R, $R_1$ and Z being as defined above:

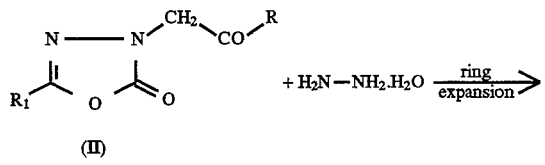

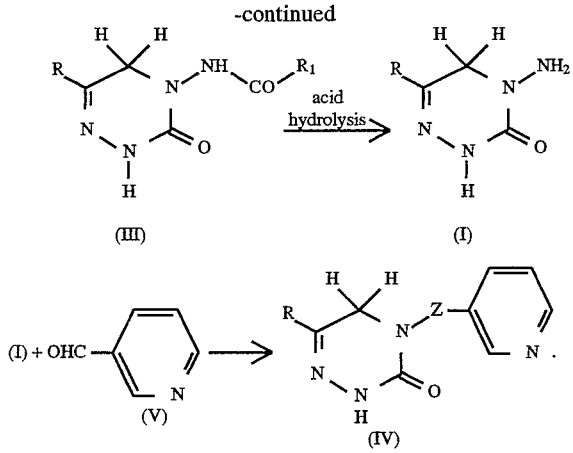

The first step (ring expansion) of the process according to the invention for the preparation of the compounds of formula I and IV is usually carried out under normal pressure and preferably in a solvent. The temperature is from +15° to +120° C., preferably from +20° to 100° C. Suitable solvents are, for example, water, nitriles, such as acetonitrile, alcohols, such as methanol, ethanol or isopropanol, and ethers such as diemethoxyethane, dioxane or tetrahydrofuran. The second step, the hydrolysis of the compounds of formula III to form the free amino compounds of formula I, is preferably carried out with inorganic acids, such as 1N hydrochloric acid to conc. hydrochloric acid or 1N to 10N sulfuric acid, at temperatures of from 0° to +120° C., especially from +20° to +100° C., in an aqueous medium or in organic solvents, such as alcohols, especially methanol or ethanol, ethers such as dioxane or tetrahydrofurannitriles, etc.. The third step, the reaction of a compound of a compound of the formula I with the compound of the formula V is preferably carried out under normal pressure, preferably in the presence of a catalytic amount of a strong acid and preferably in a solvent. The temperature is from +15° to +120° C., preferably from +40° to +80° C. Suitable acids are strong inorganic acids such as sulphuric acid and hydrochloric acid. Suitable solvents are, for example, water, nitriles, such as acetonitrile, alcohols, such as methanol, ethanol or isopropanol, ethers such as dimethoxyethane, t-butyl-methylether, dioxane or tetrahydrofuran. The reduction of the compounds of the formula is preferably carried out under normal or slightly enhanced hydrogen pressure and in a solvent. Catalysts which can be used in the hydrogenation reaction are the usual metal catalysts such as platinum-, palladium and nickel-catalysts. Alternatively, the reduction can be carried out with complex hydrides, such as $NaBH_4$ or $LiAlH_4$. Suitable solvents are, depending on whether the reduction is carried out with hydrogen or with another reduction agent, for example, water, nitriles, such as acetonitrile, alcohols, such as methanol, ethanol or isopropanol, carbonic acids such as acetic acid, esters such as acedit acid ethyl ester, or ethers such as dimethoxyethane, t-butyl-methylether, dioxane or tetrahydrofuran.

The compounds of formula III, wherein R is hydrogen, $C_1-C_6$alkyl, $C_3-C_6$cycloalkyl, $C_1-C_4$alkyl substituted by from 1 to 9 halogen atoms or by from 1 to 3 radicals selected from the group consisting of $C_1-C_3$alkoxy, $C_1-C_3$alkylthio and phenyl, phenyl or phenyl substituted by from 1 to 3 radicals selected from the group consisting of halogen, methyl, ethyl, methoxy, methylthio and nitro, and $R_1$ is hydrogen, $C_1-C_4$alkyl, $C_3-C_6$cycloalkyl, $C_1-C_4$alkyl substituted by from 1 to 9 chlorine atoms, $C_1-C_3$alkoxy, $C_1-C_3$alkylthio, $C_1-C_3$alkylsulfinyl, $C_1-C_3$alkylsulfonyl, phenyl, phenyl substituted by from 1 to 3 radicals selected from the group consisting of halogen, methyl, ethyl, methoxy, methylthio and nitro, or pyridyl, with the proviso, that R is different from unsubstituted phenyl, if $R_1$ is methyl, n-butyl, or unsubstituted phenyl, used as intermediates according to the invention are novel and also form a part of the present invention. Preferred are compounds of formula III, wherein R is methyl, ethyl, isopropyl, tert.-butyl or cyclopropyl, and compounds of formula III, wherein, in consideration of the proviso mentioned hereinbefore, $R_1$ is $C_1-C_4$alkyl.

The compounds of formula II, wherein R is hydrogen, $C_1-C_6$alkyl, $C_3-C_6$cycloalkyl, $C_1-C_4$alkyl substituted by from 1 to 9 halogen atoms or by from 1 to 3 radicals selected from the group consisting of $C_1-C_3$alkoxy, $C_1-C_3$alkylthio and phenyl, phenyl or phenyl substituted by from 1 to 3 radicals selected from the group consisting of halogen, methyl, ethyl, methoxy, methylthio and nitro, and $R_1$ is hydrogen, $C_1-C_4$alkyl, $C_3-C_6$cycloalkyl, $C_1-C_4$alkyl substituted by from 1 to 9 chlorine atoms, $C_1-C_3$alkoxy, $C_1-C_3$alkylthio, $C_1-C_3$alkylsulfinyl, $C_1-C_3$alkylsulfonyl, phenyl, phenyl substituted by from 1 to 3 radicals selected from the group consisting of halogen, methyl, ethyl, methoxy, methylthio and nitro, or pyridyl, used as starting materials according to the invention are novel and also form a part of the present invention. Preferred are compounds of formula II, wherein $R_1$ represents $C_1-C_4$-alkyl, and compounds of formula II, wherein R is methyl, ethyl, isopropyl, tert.-butyl or cyclopropyl.

The compounds of formula II can be prepared analogously to known procedures, for example as follows (see, for example, EP Patent Application No. 314,615).

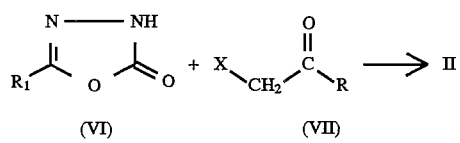

In the above formulae VI and VII, R and $R_1$ are as defined above and X is a halogen atom, preferably chlorine or bromine. The process for the preparation of the compounds of formula II is generally carried out under normal pressure, in the presence of a base and in a solvent. The temperature is from 0° to +150° C., preferably from +20° to +100° C. Suitable bases are organic and inorganic bases, for example trimethylamine, alcoholates, such as sodium methanolate, sodium hydroxide or sodium hydride. Suitable solvents are, inter alia, alcohols, such as methanol and ethanol, halogenated hydrocarbons, for example chloroform, nitriles, for example acetonitrile, tetrahydrofuran, dioxane, dimethyl sulfoxide, dimethylformamide or water.

The compounds of formula VI [see EP Patent Application No. 321,833; J. Pharm. Soc. Japan 76, 1300–1303 (1956); B. 82, 121–123 (1949)] and their preparation, and also the haloketones of formula VII, are for the most part known.

It is known from Liebigs Ann. Chem. 749, 125 ff. (1971) (C.A. Vol. 75, 129769k, 1971), Z.Chem. 1975, 219 (C.A. Vol. 83, 1315521, 1975) and the German Democratic Republic Patent No. 54369 (C.A. Vol 67, 64449u, 1967) that those 4-amino-6-phenyl-3-oxo-2,3,4,5-tetrahydro-1,2,4-triazines, which fall under the proviso mentioned hereinbefore, can be obtained starting from 2-amino-5-methyl-3-phenacyl-1,3,4-oxadiazolium bromide by reaction with hydrazine hydrate. The main disadvantage of this process is that it is limited to the preparation of 1,2,4-triazine rings that are phenyl-substituted in the 6-position; in addition, this process comprises several steps and its yield is poor. Furthermore, it is known from EP Patent Application No. 314,615 to prepare 4-amino-3-oxo-2,3,4,5-tetrahydro-1,2,4-triazines of formula Ia that are substituted in the 6-position by reacting corresponding compounds of formula IIa with an excess of hydrazine in a one-step reaction according to the reaction scheme

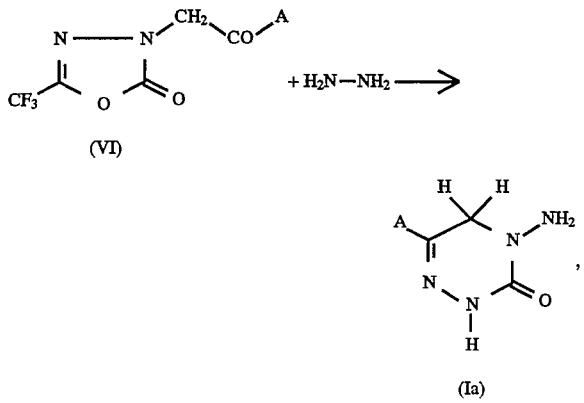

(VI)

(Ia)

wherein A may be an unsubstituted or substituted alkyl or aryl substituent. The disadvantages of this process are primarily the high cost of the trifluoroacetic acid ethyl ester required for preparing the trifluoroacethydrazide, the instability of that trifluoroacet-hydrazide at room temperature (Magn. Resonance in Chem., vol. 28, 331, 1990), and the not very high yield in the reaction of the trifluoroacethydrazide with phosgene in water (see Helv. Chim. Acta 1986, 333) to prepare the 2,3-dihydro-2-oxo-5-trifluoromethyl-1,3,4-oxadiazole from which the starting compounds of formula IIa are obtained. Moreover, the reaction according to EP Patent Application No. 314,615 inevitably produces toxic trifluoroacetic acid derivatives as a by-product, which present ecological problems and require a considerable outlay for their disposal.

In contrast, within the scope of the present invention it has now surprisingly been found that the presence of a $CF_3$-group in the 5-position of the starting compounds of formula II is not necessary for the preparation of the 4-amino-3-oxo-2,3,4,5-tetrahydro-1,2,4-triazines of formula I by ring expansion. The present starting compounds of formula II, which contain one of the mentioned radicals $R_1$ in the 5-position instead of the mentioned $CF_3$ group, react readily with hydrazine hydrate to form the acylamino compounds of formula III, from which the radical —CO—$R_1$ is subsequently removed by acid hydrolysis to obtain the compounds of formula I. With the process according to the invention, the disadvantages of the procedures hitherto available are eliminated since, in the process according to the invention, inexpensive and readily available starting compounds can be used, high yields are obtained and, instead of toxic trifluoroacetic acid derivatives, ecologically harmless carboxylic acid derivatives, for example acetic acid, are formed as a by-product.

The use of the compounds of formulae II and III in the process according to the invention forms also a part of present invention.

EXAMPLE 1

Preparation of the starting compound 2,3-dihydro-5-methyl-2-oxo-1,3,4-oxadiazol-3-yl-acetone 10 g of 2,3-dihydro-5-methyl-2-oxo-1,3,4-oxadiazole (prepared in customary manner from acethydrazide and phosgene) are added to a solution of 2.3 g of sodium in 100 ml of methanol, the mixture is stirred for a short time and then the solvent is removed in vacuo at a bath temperature of 60° C. The sodium salt so formed is introduced in portions into a solution of 9.2 g of chloroacetone and 0.2 g of tetrabutylammonium bromide in 50 ml of chloroform, and the reaction mixture is stirred for 4 hours at 65° C. After the salts have been filtered off, the solvent is removed in vacuo at a bath temperature of 50° C. The residue is recrystallized from tert.-butyl methyl ether, yielding the title compound having a melting point of 55°–58° C.

The compounds of formula II listed in table 1 can also be prepared in a manner corresponding to that described above.

TABLE 1

| $R_1$ | R | phys. data |
|---|---|---|
| H | —$CH_3$ | b.p. 0.08 torr/80° C. |
| —C($CH_3$)$_3$ | —$CH_3$ | bp. 0.07 torr/102° C. |
| 4-$NO_2$—$C_6H_4$— | —$CH_3$ | m.p. 179–181° C |
| 2-$NO_2$—$C_6H_4$— | —$CH_3$ | m.p. 98–102° C. |
| 3-$NO_2$—$C_6H_4$— | —$CH_3$ | m.p. 126–129° C. |
| 3,5-di-$NO_2$—$C_6H_3$— | —$CH_3$ | m.p. 116–118° C. |
| 2,4-di-$NO_2$—$C_6H_3$— | —$CH_3$ | m.p. 164–168° C. |
| 3-pyridyl | —$CH_3$ | m.p. 146–148° C. |
| —$CH_3$ | —$CF_3$ | |
| —H | —H | |
| —$CH_3$ | —H | |
| —$CH_3$ | —$C_2H_5$ | |
| —$CH_3$ | —CH($CH_3$)$_2$ | |
| —$CH_3$ | —C($CH_3$)$_3$ | |
| —$CH_3$ | -cyclo-$C_3H_5$ | |
| —$CH_3$ | —$C_6H_5$ | |
| —$CH_3$ | 4-Cl—$C_6H_4$— | |

EXAMPLE 2

Preparation of 4-acetylamino-6-methyl-3-oxo-2,3,4,5-tetrahydro-1,2,4-triazine a) 51.5 g of hydrazine hydrate are added to a stirred mixture of 156 g of 2,3-dihydro-5-methyl-2-oxo-1,3,4-oxadiazol-3-ylacetone in 300 g of water. The mixture is heated to 90° C. and stirred for a further 3 hours. 10 g of Amberlyst (ion exchanger) are added of the absorption of the excess hydrazine, the mixture stirred for 15 minutes and the ion exchanges filtered off. The filtrate contains 163 g of the title product (LC-analysis, 94% of the theoretical amount), which can be used in the next step without isolation.

b) To a solution of 156 g of 2,3-dihydro-5-methyl-2-oxo-1,3,4-oxadiazol-3-ylacetone in 600 ml of isopropanol and 15 ml of water, 75 g of hydrazine hydrate are added at 70° C. over a period of 30 minutes. The mixture is subsequently stirred at reflux temperature for a further 6 hours. 40 g of oxalic acid dihydrate in 160 ml of isopropanol are added, and the precipitate is filtered off, while the mixture is hot, and washed with 150 ml of isopropanol. The filtrate is evaporated in vacuo until the total volume is about 600 ml, then cooled to 0° C. to +5° C., and the precipitated product is filtered off and dried yielding 158 g (93% of the theoretical amount) of the title compound having a melting point of 199°–200° C.

The compounds of formula III listed in table 2 can also be prepared in a manner corresponding to that described above.

TABLE 2

| $R_1$ | R | melting point [°C.] |
|---|---|---|
| H | —$CH_3$ | 185–187 |
| —$C(CH_3)_3$ | —$CH_3$ | 205–207 |
| 4-$NO_2$—$C_6H_4$— | —$CH_3$ | 252–255 |
| 2-$NO_2$—$C_6H_4$— | —$CH_3$ | 255–257 |
| 3-$NO_2$—$C_6H_4$— | —$CH_3$ | 228–231 |
| 3,5-di-$NO_2$—$C_6H_3$— | —$CH_3$ | 259–262 |
| 2,4-di-$NO_2$—$C_6H_3$— | —$CH_3$ | |
| 3-pyridyl | —$CH_3$ | 259–262 |
| —$CH_3$ | —H | |
| —$CH_3$ | —$CF_3$ | |
| —H | —H | |
| —$CH_3$ | —$C_2H_5$ | |
| —$CH_3$ | —$CH(CH_3)_2$ | |
| —$CH_3$ | —$C(CH_3)_3$ | |
| —$CH_3$ | -cyclo-$C_3H_5$ | |
| —$CH_3$ | —$C_6H_5$ | |
| —$CH_3$ | -4-Cl—$C_6H_4$— | |

EXAMPLE 3

Preparation of 4-amino-6-methyl-3-oxo-2,3,4,5-tetrahydro-1,2,4-triazine a) 85 g of 4-acetylamino-6-methyl-3-oxo-2,3,4,5-tetrahydro-1,2,4-triazine in 250 ml of methanol are stirred together with 63 ml of hydrochloric acid (37%) for 4 hours at 50° C. After cooling to 5° C., 250 ml of icecold water and 125 ml of sodium hydroxide solution (50%) are added. The solvent is removed by evaporation in vacuo. The residue is taken up in 100 ml of ethanol, and the solvent is removed again in vacuo. The residue is taken up in 1200 ml of acetonitrile, undissolved salt precipitates are removed by filtration, the filtrate is concentrated to a small volume, the residue is caused to crystallize by adding 100 ml of acetic acid ethyl ester at 0° C., and the colorless crystals are filtered off and dried yielding 60.4 g (92% of the theoretical amount) of the title compound having a melting point of 118°–120° C.

b) A mixture of 85 g of 4-acetylamino-6-methyl-3-oxo-2,3,4,5-tetrahydro-1,2,4-triazine, 63 ml of hydrochloric acid (37%) and 250 ml of methanol is stirred for 4 hours at 50° C. After cooling to 15° C., 82 g of sodium acetate are added, the mixture is stirred for a further 15 minutes, and the solvent is removed by evaporation. The residue is taken up in 100 ml of ethanol, and the solvent is removed again in vacuo. The residue is taken up in 1200 ml of acetonitrile, undissolved salt precipitates are filtered off, the filtrate is evaporated to dryness, the residue is caused to crystallize by adding 50 ml of acetic acid ethyl ester at ambient temperature, and the crystals are filtered off and dried yielding 54.6 g (85% of the theoretical amount) of the title compound having a melting point of 113°–118° C.

c) A mixture of 1.7 g of 4-acetylamino-6-methyl-3-oxo-2,3,4,5-tetrahydro-1,2,4-triazine and 10 ml of 2N hydrochloric acid is stirred for 5 hours at 80° C. After cooling, 1.7 g of sodium acetate are added, and the mixture is concentrated by evaporation in vacuo at a bath temperature of 60° C. The residue is taken up in ethanol, and salt precipitates are filtered off. The filtrate is concentrated to a small volume and caused to crystallize. The title compound is obtained in the form of colorless crystals having a melting point of 116°–119° C.

The compounds of formula I listed in table 3 can also be prepared in a manner corresponding to that described above.

TABLE 3

| R | m.p. [°C.] |
|---|---|
| —$C_2H_5$ | 143–145° |
| —$C_3H_7(i)$ | 79–81° |
| —$C(CH_3)_3$ | 148–150° |
|  | 94–95° |
| 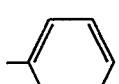 | 199–202° |
| 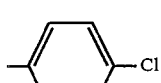 | 208–210° |
| H<br>—$CF_3$ | |

What is claimed is:

1. A process for the preparation of a compound of the formula

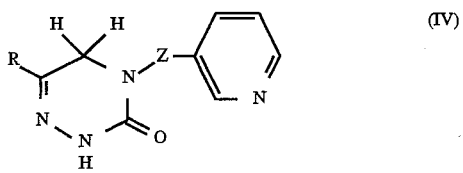

(IV)

wherein R is hydrogen, $C_1$–$C_6$alkyl, $C_3$–$C_6$cycloalkyl, $C_1$–$C_4$alkyl substituted by from 1 to 9 halogen atoms or by from 1 to 3 radicals selected from the group consisting of $C_1$–$C_3$alkoxy, $C_1$–$C_3$alkylthio and phenyl, phenyl or phenyl substituted by from 1 to 3 radicals selected from the group consisting of halogen, methyl, ethyl, methoxy, methylthio and nitro, and Z is —N=CH— or —NH—$CH_2$—, which process comprises reacting with hydrazine hydrate a compound of formula

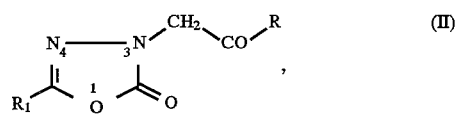

(II)

wherein $R_1$ is hydrogen, $C_1$–$C_4$alkyl, $C_3$–$C_6$cycloalkyl, $C_1$–$C_4$alkyl substituted by from 1 to 9 chlorine atoms, $C_1$–$C_3$alkoxy, $C_1$–$C_3$alkylthio, $C_1$–$C_3$alkylsulfinyl, $C_1$–$C_3$alkylsulfonyl, phenyl, phenyl substituted by from 1 to 3 radicals selected from the group consisting of halogen, methyl, ethyl, methoxy, methylthio and nitro, or pyridyl, converting the resulting compound of the formula

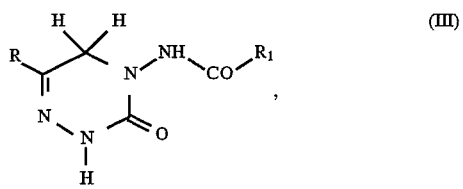

(III)

by acid hydrolysis into a compound of the formula I,

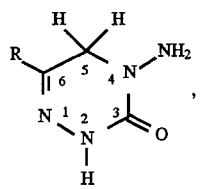

and reacting the compound of the formula I with the aldehyde of the formula

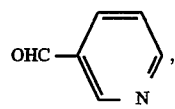

into the resulting compound of the formula IV where Z is —N=CH— or further converting by selective reduction the compound of the formula IV where Z is —N=CH— into a compound of the formula IV where Z is —NH—CH$_2$—.

2. A process according to claim 1, wherein R in the compounds of the formulae I, III and IV is selected from the group consisting of methyl, ethyl, isopropyl, tert.-butyl and cyclopropyl.

3. A process according to claim 1, wherein $R_1$ is $C_1$–$C_4$-alkyl.

4. A process according to claim 2, wherein $R_1$ is $C_1$–$C_4$-alkyl.

5. A process according to claim 1, wherein the compound of formula II is reacted with hydrazine hydrate at a temperature of from about +15° C. to +120° C.

6. A process according to claim 1, wherein the compound of formula II is reacted with hydrazine hydrate in an alcohol as solvent.

7. A process according to claim 1, wherein the hydrolisis of the compound of formula III is acid hydrolysis.

8. A process according to claim 7, wherein the acid hydrolysis is an inorganic acid hydrolisis.

9. A process according to claim 1, wherein the hydrolisis of the compound of formula III is carried out at a temperature from about +15° C. to +120° C.

10. A process according to claim 1, wherein the hydrolisis of the compound of formula III is carried out in water, in an alcohol, or in a mixture of water and an alcohol.

11. A process according to claim 1, wherein the compound of the formula II is 2,3-dihydro-5-methyl-2-oxo-1,3,4-oxadiazol-3-yl-acetone.

12. A process according to claim 1, wherein the compound of formula III is 4-acetylamino-6-methyl-3-oxo-2,3,4,5-tetrahydro-1,2,4-triazine.

13. A process according to claim 1 wherein the compound of the formula IV is 4-acetylamino-6-methyl-3-oxo-2,3,4,5-tetrahydro-1,2,4-triazine.

* * * * *